US00PP20595P2

(12) United States Plant Patent
Thompson

(10) Patent No.: US PP20,595 P2
(45) Date of Patent: Dec. 22, 2009

(54) ***HYDRANGEA* PLANT NAMED 'SONMARIE'**

(50) Latin Name: *Hydrangea macrophylla*
Varietal Denomination: Sonmarie

(75) Inventor: Tony Thompson, Kingston Springs, TN (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/287,025

(22) Filed: Oct. 1, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Susan B McCormick Ewoldt
(74) *Attorney, Agent, or Firm*—C. A. Whealy

(57) ABSTRACT

A new and distinct cultivar of *Hydrangea* plant named 'Sonmarie', characterized by its relatively compact, upright and mounded plant habit; strong and sturdy stems; and large hemispherical inflorescences with numerous light red purple-colored sterile flowers.

1 Drawing Sheet

Botanical designation: *Hydrangea macrophylla.*
Cultivar denomination: 'Sonmarie'.

BACKGROUND OF THE INVENTION

The present invention relates to a new and distinct cultivar of *Hydrangea*, botanically known as *Hydrangea macrophylla* and hereinafter referred to by the name 'Sonmarie'.

The new *Hydrangea* is a naturally-occurring whole plant mutation of an unnamed selection of *Hydrangea macrophylla*, not patented. The new *Hydrangea* was discovered and selected by the Inventor in 1998 as a single flowering plant within a population of plants of the unnamed selection in a controlled outdoor nursery environment in Nashville, Tenn.

Asexual reproduction of the new cultivar by softwood cuttings in a controlled environment in Kingston, Tenn. since 2001 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sonmarie'. These characteristics in combination distinguish 'Sonmarie' as a new and distinct cultivar of *Hydrangea:*

1. Relatively compact, upright and mounded plant habit.
2. Strong and sturdy stems.
3. Large hemispherical inflorescences with numerous light red purple-colored sterile flowers. Plants of the new *Hydrangea* differ from plants of the parent selection primarily in plant size as plants of the new *Hydrangea* are more compact than plants of the parent selection.

Plants of the new *Hydrangea* can be compared to plants of *Hydrangea macrophylla* 'Alpenglow', not patented. Plants of the new *Hydrangea* differ from plants of 'Alpenglow' in the following characteristics:

1. Plants of the new *Hydrangea* are more compact than and not as vigorous as plants of 'Alpenglow'.
2. Plants of the new *Hydrangea* are more freely branching than plants of 'Alpenglow'.
3. Plants of the new *Hydrangea* have stronger and sturdier stems than plants of 'Alpenglow'.
4. Plants of the new *Hydrangea* have smaller leaves than plants of 'Alpenglow'.
5. Inflorescences of plants of the new *Hydrangeas* had more flowers than inflorescences of plants of 'Alpenglow'.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph at the bottom of the sheet comprises a side perspective view of a typical flowering plant of 'Sonmarie' grown in an outdoor nursery.

The photograph at the top of the sheet is a close-up view of a typical inflorescence of 'Sonmarie'.

DETAILED BOTANICAL DESCRIPTION

Plants used for the aforementioned photographs and the following description were grown during the spring in Grand Haven, Mich. in ground beds in a polyethylene-covered greenhouse and under conditions which closely approximate commercial production conditions. Plants of the new *Hydrangea* had been growing for two years when the photographs and description were taken. In the following description, color references are made to The Royal Horticultural Society Colour Chart, 1995 Edition, except where general terms of ordinary dictionary significance are used.

Botanical description: *Hydrangea macrophylla* 'Sonmarie'.

Parentage: Naturally-occurring whole plant mutation of an unnamed selection of *Hydrangea macrophylla*, not patented.

Propagation:

*Type cutting.*—By softwood cuttings.

*Time to initiate roots.*—About 10 days at temperatures of about 24° C.

*Time to produce a rooted young plant.*—About two months at temperatures of about 24° C.

*Root description.*—Fibrous.

*Rooting habit.*—Freely branching; dense.

Plant description:

*Form/growth habit.*—Perennial shrub. Relatively compact, upright and mounded plant habit. Strong and sturdy lateral branches; low vigor to moderately vigorous growth habit.

*Plant height.*—About 34 cm.

*Plant diameter or area of spread.*—About 39 cm.

*Branching habit.*—Freely branching habit with about 25 lateral branches developing per plant; pinching enhances lateral branch development.

*Lateral branches.*—Length: About 26 cm. Diameter: About 5 mm. Internode length: About 4.3 cm. Texture: Smooth, glabrous. Strength: Strong, sturdy. Color, young: Close to 144A; random markings, about 1 mm by 2 mm in size, close to 184A in color. Color, mature: Close to 197B.

Foliage description:

*Arrangement.*—Opposite, simple.

*Length.*—About 9.5 cm.

*Width.*—About 5.5 cm.

*Shape.*—Ovate.

*Apex.*—Acute.

*Base.*—Obtuse.

*Margin.*—Serrate.

*Texture, upper and lower surfaces.*—Smooth, glabrous; leathery.

*Venation pattern.*—Pinnate.

*Color.*—Developing and fully expanded leaves, upper surface: Close to 139A; venation, close to 139C. Developing and fully expanded leaves, lower surface: Close to 139B; venation, close to 139D.

*Petioles.*—Length: About 1.5 cm. Diameter: About 4 mm. Texture, upper and lower surfaces: Smooth, glabrous. Color, upper surface: Close to 139C. Color, lower surface: Close to 139D.

Flower description:

Flower type and habit.—Single sterile and fertile flowers arranged on terminal hemispherical panicles. Flowers face upright or outward.

Fragrance, fertile and sterile flowers.—None detected.

Natural flowering season.—Continuous flowering from June until frost in the fall in Grand Haven, Mich.

*Flower longevity, fertile flowers.*—Flowers last about one week on the plant; flowers persistent.

*Flower longevity, sterile flowers.*—Flowers last from June until frost on the plant; flowers persistent.

*Quantity of flowers.*—Freely flowering; about 32 fertile flowers and about 192 sterile flowers per panicle.

*Panicle height.*—About 11 cm.

*Panicle diameter.*—About 16 cm.

*Flower diameter, fertile flowers.*—About 8 mm.

*Flower depth (height), fertile flowers.*—About 4 mm.

*Flower diameter, sterile flowers.*—About 3.2 cm.

*Flower depth (height), sterile flowers.*—About 8 mm.

*Flower buds, fertile and sterile flowers.*—Length: About 4 mm. Diameter: About 3 mm. Shape: Globose. Color: Close to 142B.

*Petals, fertile flowers only.*—Arrangement: About four to five in a single star-shaped whorl. Length: About 4 mm. Width: About 3 mm. Shape: Lanceolate, cupped. Apex: Acute. Base: Attenuate. Margin: Entire. Texture, upper and lower surfaces: Smooth, glabrous. Color: When opening, upper and lower surfaces: Close to 58D. Fully opened, upper and lower surfaces: Close to 58D.

*Sepals, fertile flowers.*—Quantity per flower: About six in a single whorl, fused at base. Length: About 1 mm. Width: About 0.5 mm. Shape: Roughly ovate. Apex: Acute. Margin: Entire. Texture, upper and lower surfaces: Smooth, glabrous. Color: When opening, upper and lower surfaces: Close to 142D. Fully opened, upper and lower surfaces: Close to 142D.

*Sepals, sterile flowers.*—Quantity per flower: About four in a single whorl. Length: About 1.8 cm. Width: About 1.8 cm. Shape: Ovate to deltoid. Apex: Acute. Base: Truncate. Margin: Entire. Texture, upper and lower surfaces: Smooth, glabrous. Color: When opening, upper and lower surfaces: Close to 142C. Fully opened, upper surface: Close to 58B. Fully opened, lower surface: Close to 58D.

*Peduncles, fertile and sterile flowers.*—Angle: Erect. Strength: Moderately strong, sturdy. Length: About 2.1 cm. Diameter: About 2 mm. Texture: Smooth, glabrous. Color: Close to 142C.

*Pedicels, fertile flowers.*—Angle: Erect to about 10° from vertical. Strength: Moderately strong. Length: About 4 mm. Diameter: About 2 mm. Texture: Smooth, glabrous. Color: Close to 142C.

*Pedicels, sterile flowers.*—Angle: Erect to about 20° from vertical. Strength: Moderately strong. Length: About 8 mm. Diameter: About 2 mm. Texture: Smooth, glabrous. Color: Close to 142C.

*Reproductive organs, fertile flowers only.*—Stamens: Quantity per flower: About ten. Anther shape: Oblong. Anther length: About 0.5 mm. Anther color: Close to 155D. Pollen amount: Moderate. Pollen color: Close to 155D. Pistils: Pistil quantity per flower: About two. Pistil length: About 2 mm. Stigma shape: Bi-lobed. Stigma color: Close to 144D. Style length: About 1 mm. Style color: Close to 144D. Ovary color: Close to 144D.

*Seeds.*—Quantity per inflorescence: Numerous. Size: Less than 0.1 mm by less than 0.1 mm. Color: Close to 200D.

Disease/pest resistance: Plants of the new *Hydrangea* have not been observed to be resistant to pests or pathogens common to *Hydrangea*.

Temperature tolerance: Plants of the new *Hydrangea* have been shown to be tolerant to temperatures ranging from about −29° C. to about 37° C.

It is claimed:

1. A new and distinct *Hydrangea* plant named 'Sonmarie' as illustrated and described.

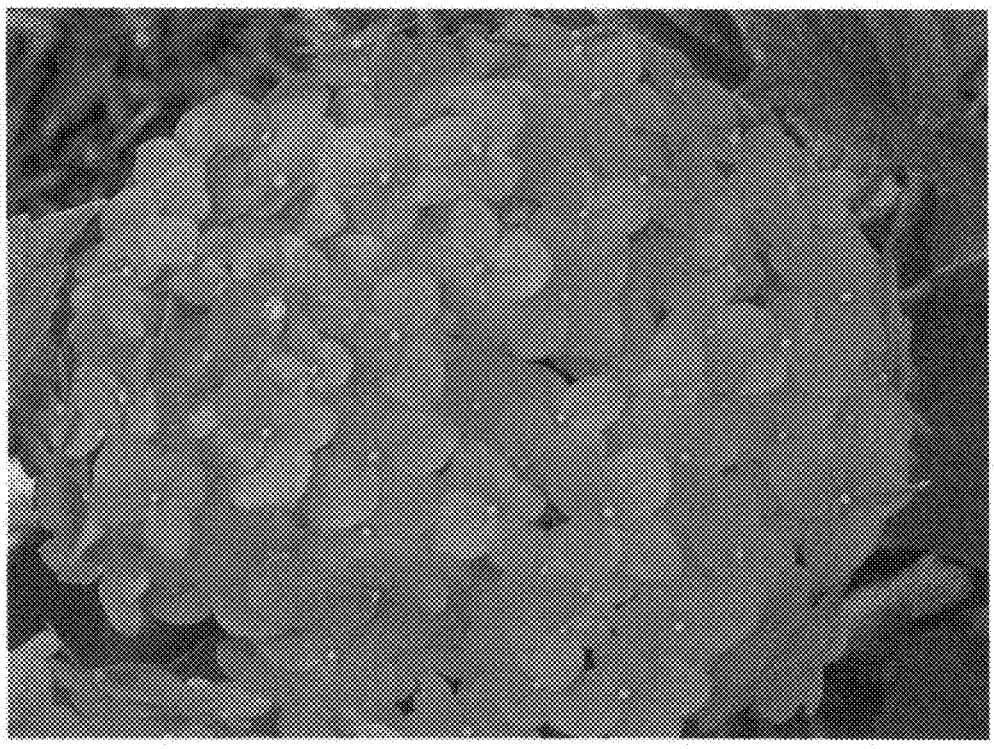
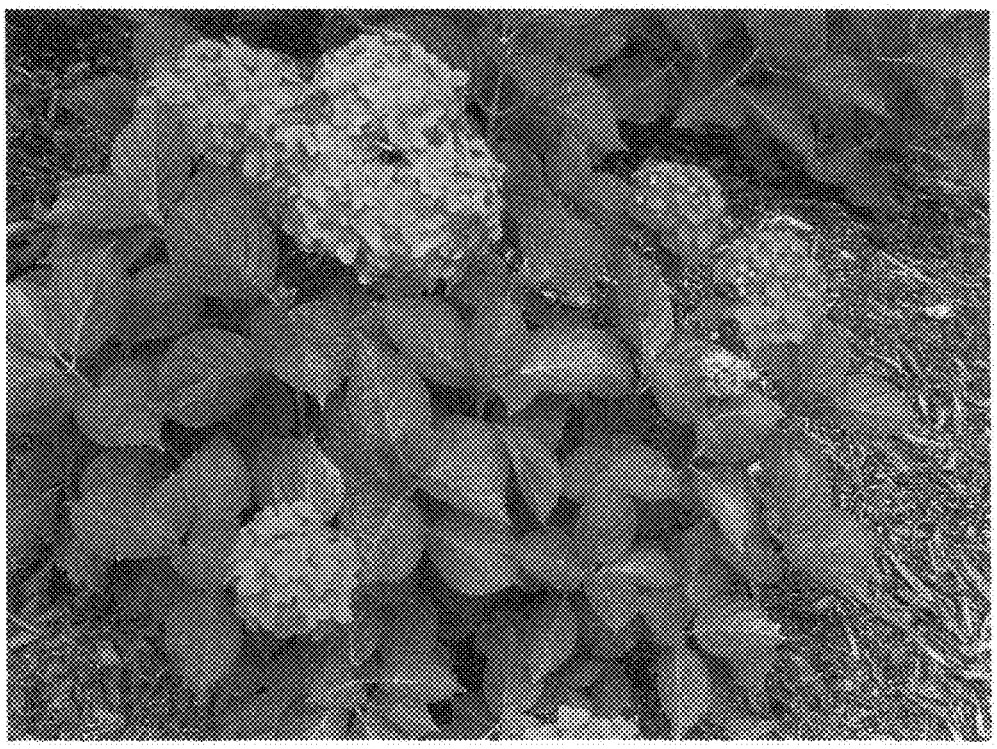

* * * * *